(12) United States Patent
Budd

(10) Patent No.: US 8,539,790 B1
(45) Date of Patent: Sep. 24, 2013

(54) SECURE CLIMATE-CONTROL SYSTEM

(76) Inventor: Randy L. Budd, Gilbert, AZ (US)

( * ) Notice: Subject to any disclaimer, the term of this patent is extended or adjusted under 35 U.S.C. 154(b) by 2332 days.

(21) Appl. No.: 10/955,074

(22) Filed: Sep. 29, 2004

Related U.S. Application Data

(60) Provisional application No. 60/525,398, filed on Nov. 26, 2003.

(51) Int. Cl.
*F25D 11/00* (2006.01)

(52) U.S. Cl.
USPC .................................................... 62/457.9

(58) Field of Classification Search
USPC .................. 705/22; 62/3.6, 457.9, 3.61, 371, 62/440, 457.1, 3, 6
See application file for complete search history.

(56) References Cited

U.S. PATENT DOCUMENTS

| | | | | |
|---|---|---|---|---|
| 4,573,581 A | * | 3/1986 | Galloway et al. | 206/570 |
| 4,669,696 A | * | 6/1987 | Petta | 248/550 |
| 5,217,064 A | | 6/1993 | Kellow et al. | |
| 5,291,746 A | * | 3/1994 | Abbott | 62/89 |
| 5,572,873 A | | 11/1996 | Lavigne et al. | |
| 5,661,978 A | * | 9/1997 | Holmes et al. | 62/3.6 |
| 5,924,289 A | | 7/1999 | Bishop, II | |
| 5,946,929 A | * | 9/1999 | Selina et al. | 62/263 |
| 6,220,049 B1 | * | 4/2001 | Lajeunesse | 62/440 |
| 6,354,104 B1 | | 3/2002 | Feagin | |
| 6,367,280 B1 | * | 4/2002 | Funabasama et al. | 62/454 |
| 6,461,234 B1 | * | 10/2002 | Kretzer | 454/237 |
| 6,543,250 B1 | * | 4/2003 | Mills et al. | 62/428 |
| 7,043,935 B2 | * | 5/2006 | Hunter | 62/457.2 |
| 2002/0053213 A1 | | 5/2002 | Lajeunesse | |
| 2003/0102685 A1 | * | 6/2003 | Sioutis | 296/24.1 |
| 2003/0126030 A1 | * | 7/2003 | Hungerford, III | 705/26 |

* cited by examiner

*Primary Examiner* — Marc Norman
(74) *Attorney, Agent, or Firm* — Stoneman Law Patent Group; Martin L. Stoneman

(57) ABSTRACT

A secure climate-control system for improved storage of substances transported by emergency response vehicles that require controlled-temperature storage, particularly drugs, blood, and physiological samples. It includes a lockable, temperature controlled cabinet permanently connected to the emergency response vehicle. The lockable storage compartment may contain lockable containers, providing double-lock security.
Business methods comprising designing, manufacturing, installing, and using custom secure climate-control systems are also disclosed.

35 Claims, 12 Drawing Sheets

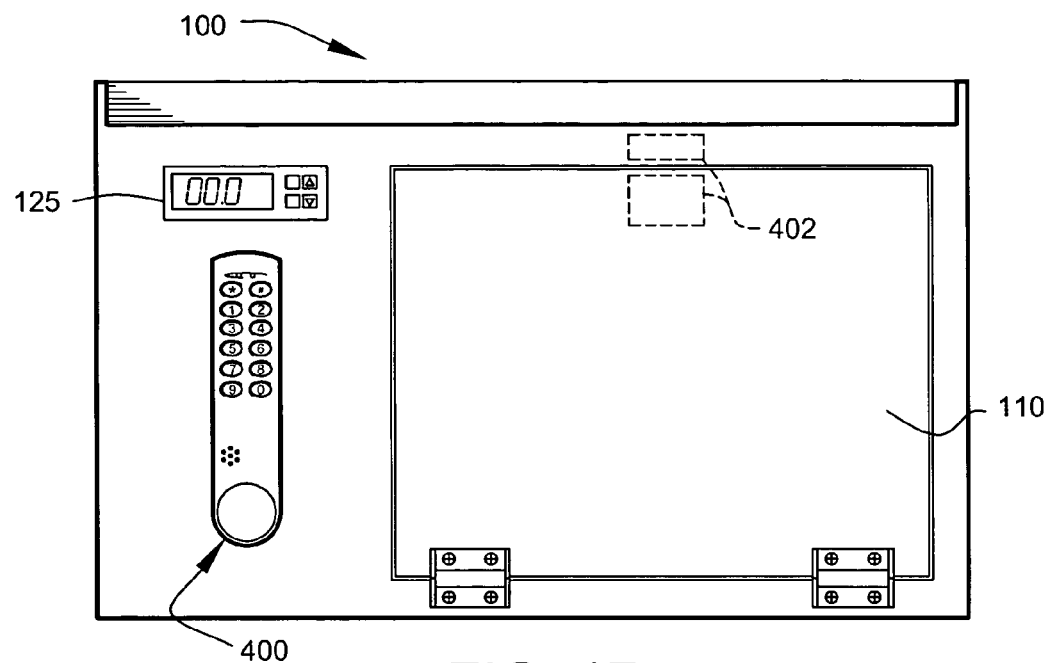
FIG. 17
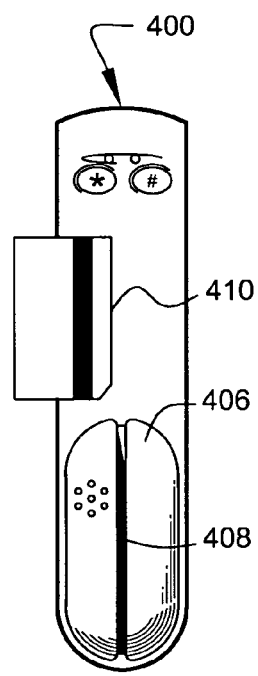 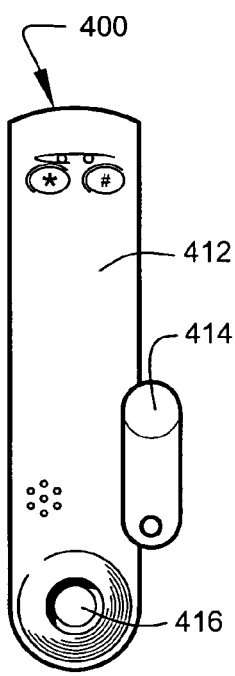 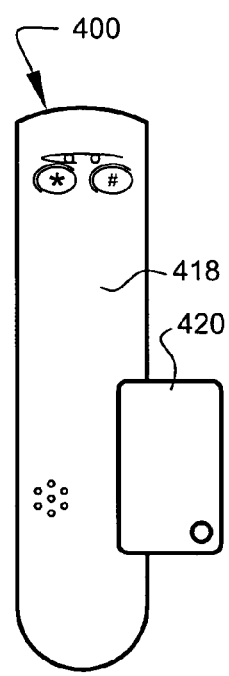 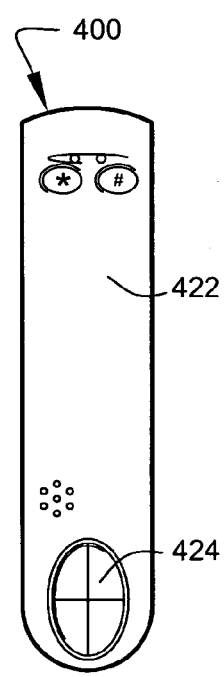
FIG. 18   FIG. 19   FIG. 20   FIG. 21

SECURE CLIMATE-CONTROL SYSTEM

CROSS-REFERENCE TO RELATED APPLICATION

The present application is related to and claims priority from prior provisional application Ser. No. 60/525,398, filed Nov. 26, 2003, entitled "SECURE CLIMATE-CONTROL SYSTEM", the contents of which are incorporated herein by this reference and are not admitted to be prior art with respect to the present invention by the mention in this cross-reference section.

BACKGROUND

This invention relates to providing a system for improved storage of substances transported by emergency response vehicles that require controlled-temperature storage, particularly of drugs, blood, and physiological samples.

Typically, emergency response vehicles (hereinafter called "ERV"s), such as ambulances, fire rescue vehicles, and fire engines, carry lifesaving equipment and medical supplies. The temperature in an ERV can vary from well below freezing to well over 100 degrees Fahrenheit, depending on the time of year.

Some medical supplies include drugs that require controlled-climate storage to keep their potency. Other medical supplies include blood, plasma, and intravenous solutions that require controlled cold storage to prevent spoilage. Still other medications, such as epinephrine, require storage at controlled room temperature. Some drugs lose their potency if they are frozen. Even drugs and supplies without specific climate-control instructions are preferably stored at a controlled room temperature.

Frequently, life-saving drugs are legally controlled substances, such as morphine, which must legally be kept under lock and key to prevent access by unauthorized persons. Some controlled substances are necessarily or preferably kept in climate-controlled storage, including such drugs as the anti-seizure drug lorazepam.

At present, due to factors including the varying temperature and security requirements of medical supplies used by the crews of ERVs, drugs may be stored in several different locations throughout the ERV. This factor alone complicates access to the drugs in an emergency.

Emergency response technicians without proper, secure, controlled-storage systems may not be able to carry and use temperature-sensitive controlled drugs for their emergency patients, resulting in poorer service to emergency patients.

A lockable, climate-controlled storage device, which is securely installed on an emergency response vehicle, is needed in order to safely, conveniently, and securely store temperature-sensitive controlled substances on emergency response vehicles.

OBJECTS AND FEATURES OF THE INVENTION

A primary object and feature of the present invention is to provide a secure climate-control system. It is a further primary object and feature of the present invention to provide a secure potency-preservation apparatus.

It is a further object and feature of the present invention to provide such a system and apparatus that can provide heating or cooling action to maintain an essentially constant temperature. It is yet a further object and feature of the present invention to provide such a system and apparatus with multiple closable compartments. It is yet a further object and feature of the present invention to provide such a system and apparatus with multiple climate-controlled closable compartments. It is yet a further object and feature of the present invention to provide such a system and apparatus with multiple independently-climate-controlled closable compartments.

It is a further object and feature of the present invention to provide such a system and apparatus with independently-lockable internal containers.

Yet another object and feature of the present invention is to provide such a system and apparatus capable of operating on any of several different power sources.

A further object and feature of the present invention is to provide a business method comprising custom-designing and building secure potency-preservation apparatus for permanent installation on emergency response vehicles. Yet a further object and feature of the present invention is to provide a business method comprising using such custom secure climate-control systems to transport medical supplies and/or controlled substances.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a secure climate-control system, for preserving potency of at least one controlled substance on at least one wheeled emergency-response transport, comprising: at least one secure potency-preserver structured and arranged to securely preserve potency of such at least one controlled substance; and at least one permanent connector adapted to permanently connect such at least one secure potency-preserver onto the at least one wheeled emergency-response transport.

Moreover, it provides such a secure climate-control system, wherein such at least one secure potency-preserver comprises: at least one closable compartment adapted to enclose at least one controlled substance; wherein such at least one closable compartment comprises at least one openable access; at least one temperature controller adapted to control at least one user-definable temperature of such at least one closable compartment; at least one lock to lock such at least one openable access in a closed position to prevent unauthorized access to such at least one closable compartment.

Additionally, it provides such a secure climate-control system, further comprising at least one wheeled emergency-response transport adapted to land-transport emergency-response personnel and controlled substances to emergency situations. Also, it provides such a secure climate-control system, wherein such at least one temperature controller comprises at least one temperature indicator structured and arranged to indicate at least one temperature of such at least one closable compartment. In addition, it provides such a secure climate-control system, wherein such at least one temperature indicator comprises at least one thermometer. And, it provides such a secure climate-control system, wherein such at least one temperature controller comprises at least one thermostat. Further, it provides such a secure climate-control system, wherein such at least one temperature controller comprises at least one temperature adjuster structured and arranged to adjust at least one temperature of such at least one closable compartment. Even further, it provides such a secure climate-control system, further comprising at least one heat sink structured and arranged to dissipate excess heat. Moreover, it provides such a secure climate-control system, further comprising at least one vent structured and arranged to dissipate excess heat.

Additionally, it provides such a secure climate-control system, further comprising at least one fan structured and arranged to dissipate excess heat. Also, it provides such a secure climate-control system, further comprising at least one humidity controller structured and arranged to control at least one humidity level in such at least one closable compartment. In addition, it provides such a secure climate-control system, further comprising at least one insulator structured and arranged to insulate such at least one closable compartment. And, it provides such a secure climate-control system, wherein such at least one insulator comprises at least one vacuum insulator structured and arranged to insulate such at least one closable compartment.

Further, it provides such a secure climate-control system, wherein such at least one insulator comprises at least one foam insulator structured and arranged to insulate such at least one closable compartment. Even further, it provides such a secure climate-control system, wherein such at least one insulator comprises at least one plastic insulator structured and arranged to insulate such at least one closable compartment.

Moreover, it provides such a secure climate-control system, further comprising at least one cover structured and arranged to cover at least such at least one closable compartment and such at least one temperature controller. Additionally, it provides such a secure climate-control system, wherein such at least one cover comprises at least one metal. Also, it provides such a secure climate-control system, wherein such at least one openable access comprises at least one door. In addition, it provides such a secure climate-control system, further comprising at least one locking latch structured and arranged to latch and lock such at least one door. And, it provides such a secure climate-control system, further comprising at least one seal structured and arranged to seal such at least one door against such at least one closable compartment.

Further, it provides such a secure climate-control system, further comprising at least one hinge structured and arranged to hingedly connect such at least one door with such at least one cover. Even further, it provides such a secure climate-control system, further comprising at least one container structured and arranged to contain at least one medical supplies, wherein such at least one container is adapted to be inserted into such at least one closable compartment. Moreover, it provides such a secure climate-control system, wherein such at least one container comprises at least one lock, structured and arranged to lock such at least one container. Additionally, it provides such a secure climate-control system, wherein such at least one lock comprises: at least one electrically-actuated latch; and at least one latch controller.

Also, it provides such a secure climate-control system, wherein such at least one latch controller comprises: at least one electric switch adapted to actuate such at least one electrically-actuated latch; wherein such at least one electric switch is located within a first portion of the at least one wheeled emergency-response transport; and wherein such at least one electric switch is remotely located within a second portion of the at least one wheeled emergency-response transport.

In addition, it provides such a secure climate-control system, wherein: such at least one latch controller comprises at least one electronic device structured and arranged to control at least one locking function of such at least one electrically-actuated latch; and such at least one electronic device is structured and arrange to control such at least one locking function on receiving at least one electronic authentication. And, it provides such a secure climate-control system, wherein such at least one electronic device performs such at least one electronic authentication by receiving at least one authenticating key code from at least one keypad. Further, it provides such a secure climate-control system, wherein such at least one electronic device performs such at least one electronic authentication by analyzing at least one biometric identifier. Even further, it provides such a secure climate-control system, wherein such at least one electronic device performs such at least one electronic authentication by acquiring authentication data from at least one data-containing device. Moreover, it provides such a secure climate-control system, wherein such at least one data-containing device comprises at least one magnetic stripe. Additionally, it provides such a secure climate-control system, wherein such at least one data-containing device is adapted to provide such at least one electronic authentication by wireless means. Also, it provides such a secure climate-control system, wherein such at least one electronic device comprises at least one data memory adapted to store authentication data. In addition, it provides such a secure climate-control system, wherein such at least one electronic device comprises at least one data port adapted to permit external access to such stored authentication data by at least one portable data transfer device.

In accordance with another preferred embodiment hereof, this invention provides a method of doing business comprising the steps of: designing at least one secure potency-preserver, wherein such at least one secure potency-preserver is structured and arranged to be connected on at least one type of emergency-response vehicle in at least one specified location; receiving at least one order for such at least one secure potency-preserver; manufacturing such at least one secure potency-preserver; and installing such at least one secure potency-preserver on such at least one emergency-response vehicle.

In accordance with another preferred embodiment hereof, this invention provides a method of doing business comprising the steps of: designing at least one secure potency-preserver, wherein such at least one secure potency-preserver is structured and arranged to fit at least one of a large number of similar emergency response vehicles owned or operated by at least one governing authority; receiving at least one order for such at least one secure potency-preserver from such at least one governing authority; manufacturing such at least one secure potency-preserver; and installing such at least one secure potency-preserver on such at least one of such large number of similar emergency response vehicles owned or operated by such at least one governing authority.

In accordance with another preferred embodiment hereof, this invention provides a method of doing business comprising the step of transporting medical supplies in at least one closable compartment of at least one secure potency-preserver, wherein such at least one secure potency-preserver is permanently installed on at least one emergency response vehicle. In accordance with yet another preferred embodiment hereof, this invention provides a method of doing business comprising the step of transporting medical supplies in at least one closable compartment of at least one secure climate-control system.

BRIEF DESCRIPTION OF THE DRAWINGS

FIG. 17 illustrates a front view of a secure climate-controller according to a preferred embodiment of the present invention.

FIG. 18 illustrates a front view of a card swipe lock used to access the secure climate-controller according to a preferred embodiment of the present invention.

FIG. 19 illustrates a front view of a digital touch-key lock used to access secure the climate-controller according to a preferred embodiment of the present invention.

FIG. 20 illustrates a front view of a proximity card lock used to access the secure climate-controller according to a preferred embodiment of the present invention.

FIG. 21 illustrates a front view of a biometrically keyed lock used to access the secure climate-controller according to a preferred embodiment of the present invention.

DETAILED DESCRIPTION OF THE BEST MODES AND PREFERRED EMBODIMENTS OF THE INVENTION

Figure 1A:
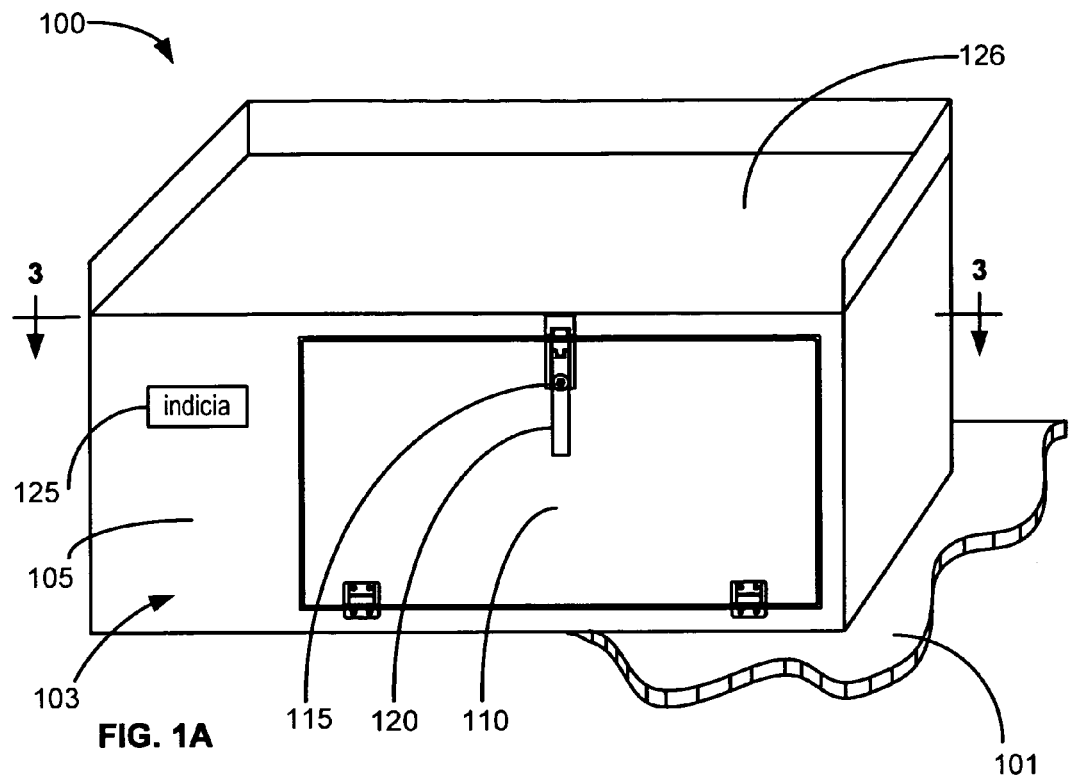
FIG. 1A illustrates a perspective view of a potency-preservation apparatus according to a preferred embodiment of the present invention.
Figure 1B:
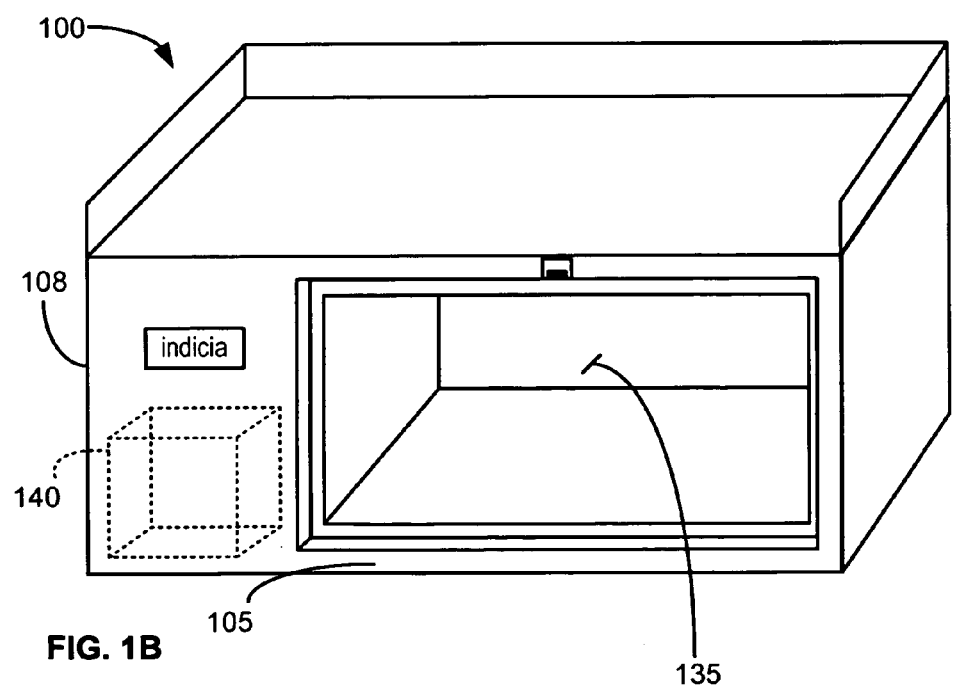
FIG. 1B illustrates a perspective view of the potency-preservation apparatus of FIG. 1A with the door removed.

FIGS. 1A and 1B illustrate a perspective view of a secure climate-controller 100 according to a preferred embodiment of the present invention. Preferably, secure climate-controller 100 includes cover 105, door 110, lock 115, latch 120, temperature indicator 125, and tray top 126, as shown. Preferably, behind door 110 is closable compartment 135, suitable for storing medical supplies or samples, as shown. Preferably, concealed behind cover 105 on the left side 108 of secure climate-controller 100 is temperature controller 140, as shown. Preferably, temperature controller 140 acts to maintain an essentially constant selected temperature in closable compartment 135 of secure climate-controller 100. Secure climate-controller 100 is preferably permanently installed on an emergency response vehicle 101, as shown especially in FIG. 12. Secure climate-controller 100 is preferably custom designed to be installed in an available space on an emergency response vehicle 101, as shown. Such emergency response vehicle 101 ("ERV 101") may be any wheeled emergency-response transport adapted to land-transport emergency response personnel and controlled substances to emergency situations, such as, for example, an ambulance, fire-rescue vehicle, fire engine, veterinary vehicle, other land-based rescue vehicle, or other land-based medical transport vehicle (at least embodying herein wheeled emergency response transport means for land-transporting emergency response personnel and controlled substances to emergency situations). The space available varies depending on the individual ERV 101 and the other equipment installed on that ERV 101, so secure climate-controller 100 will typically be custom designed to fit as desired by the ERV authority.

Secure climate-controller 100 preferably permits climate-controlled, secure transport of items such as drugs, blood, toxicology samples, criminal evidence, and controlled substances (at least embodying herein secure potency-preserving means for securely preserving potency of such controlled substances). Controlled substances are defined as chemicals listed in Schedules I through V of the Controlled Substances Act (21 U.S.C. 812) and in related Federal legislation and regulations. It should be noted that the term "Controlled Substance", as used within the teachings of this specification, shall be understood to include within its definition, any material used in emergency response operations including but not limited to; temperature sensitive equipment/materials, hazardous equipment/materials, any material or apparatus requiring the monitoring of consumption or use, etc.

Figure 2A:
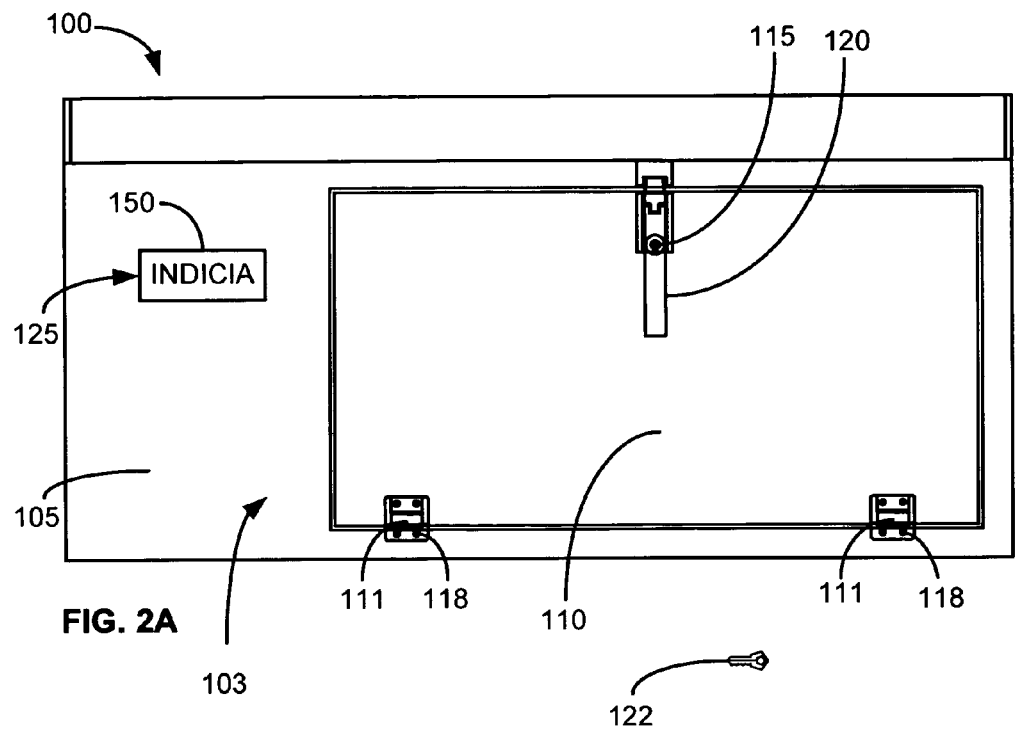
FIG. 2A illustrates a front view of the potency-preservation apparatus of FIG. 1A.
Figure 2B:
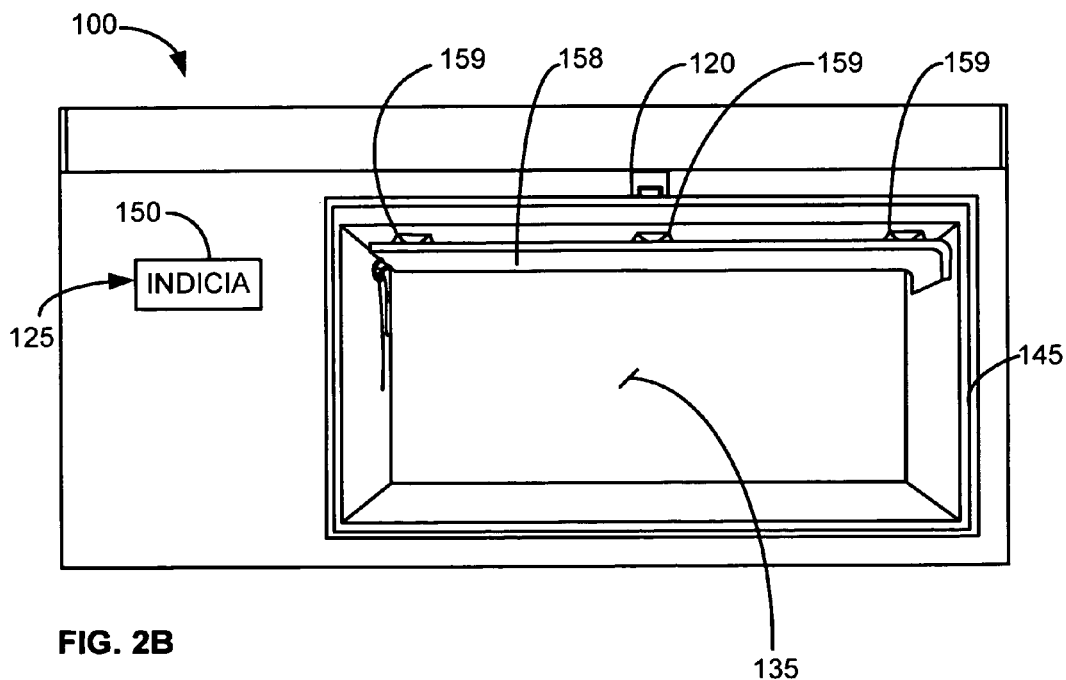
FIG. 2B illustrates a front view of the potency-preservation apparatus of FIG. 1A with the door removed.

FIGS. 2A and 2B illustrate front views of the secure climate-control system of FIGS. 1A and 1B. Preferably, door 110 is designed to fit flush with cover 105, and seals tightly against the opening of closable compartment 135, as shown. Preferably, seal 145 assists the airtight seal between door 110 and closable compartment 135. Preferably, door 110 is insulated to help maintain the regulated temperature of closable compartment 135, as shown.

Preferably, door 110 has at least one handle, which, in this preferred embodiment, comprises latch 120, as shown. Preferably, latch 120 is a compression latch. Most preferably, latch 120 is a high-compression latch comprising lock 115, preferably the over-center lever latch, part number A7-10-302-75, manufactured by Southco of Concordville, Pa., as shown (at least embodying herein lock means for locking said openable access means in a closed position to prevent unauthorized access to said closable compartment means). Lock 115 preferably opens with key 122, as shown, but may be a combination-openable or other type of lock as described in greater detail below. Preferably, latch 120 is locked when not being accessed, as shown. Upon reading this specification, those of skill in the art will understand that, under appropriate circumstances, such as user preference, advances in technology, legal requirements, etc., other door arrangements, such as multiple locks on one door, doors not flush with the cover, other types of handles, other types of locks, etc., may suffice.

Preferably, door 110 is hingedly connected to cover 105 with one or more hinges 111, as shown. Preferably, door 110 may be arranged to open in any direction required by the user (at least embodying herein wherein said closable compartment means comprises openable access means). In this preferred embodiment, door 110 opens downward, as shown. Preferably, hinges 111 are constant-torque friction hinges, preferably those manufactured by Southco of Concordville, Pa., as shown. Constant-torque friction hinges 111 preferably keep door 110 open when closable compartment 135 is being accessed, as shown. Hinges 111 are preferably fastened with permanent connectors 118, as shown, further described below. Upon reading this specification, those of skill in the art will understand that, under appropriate circumstances, such as user preference, advances in technology, installation requirements, etc., other hinges and hinge placements, such as interior hinges, hinges placed to open the door to the side, hinges placed to open the door upward, rubber gasket hinges, metal hinges, plastic hinges, etc., may suffice.

Preferably, temperature indicator 125 is placed on the front 103 of secure climate-controller 100, where it can be easily seen, as shown. Temperature indicator 125 is preferably a digital readout of digital thermometer 150, which is preferably arranged to measure the temperature inside closable compartment 135, as shown. Preferably, digital thermometer 150 also comprises a user-programmable thermostat to control the temperature in closable compartment 135, in conjunction with temperature controller 140. Upon reading this specification, those of skill in the art will understand that, under appropriate circumstances, such as user preference, advances in technology, etc., other temperature indicating systems, such as analog thermometers, color-changing displays, audible signals, linking to a data storage device that records the temperature in the closable compartment over time (in order to provide proof that temperature-sensitive substances have been maintained at the correct temperature in storage), etc., may suffice.

Figure 3A:
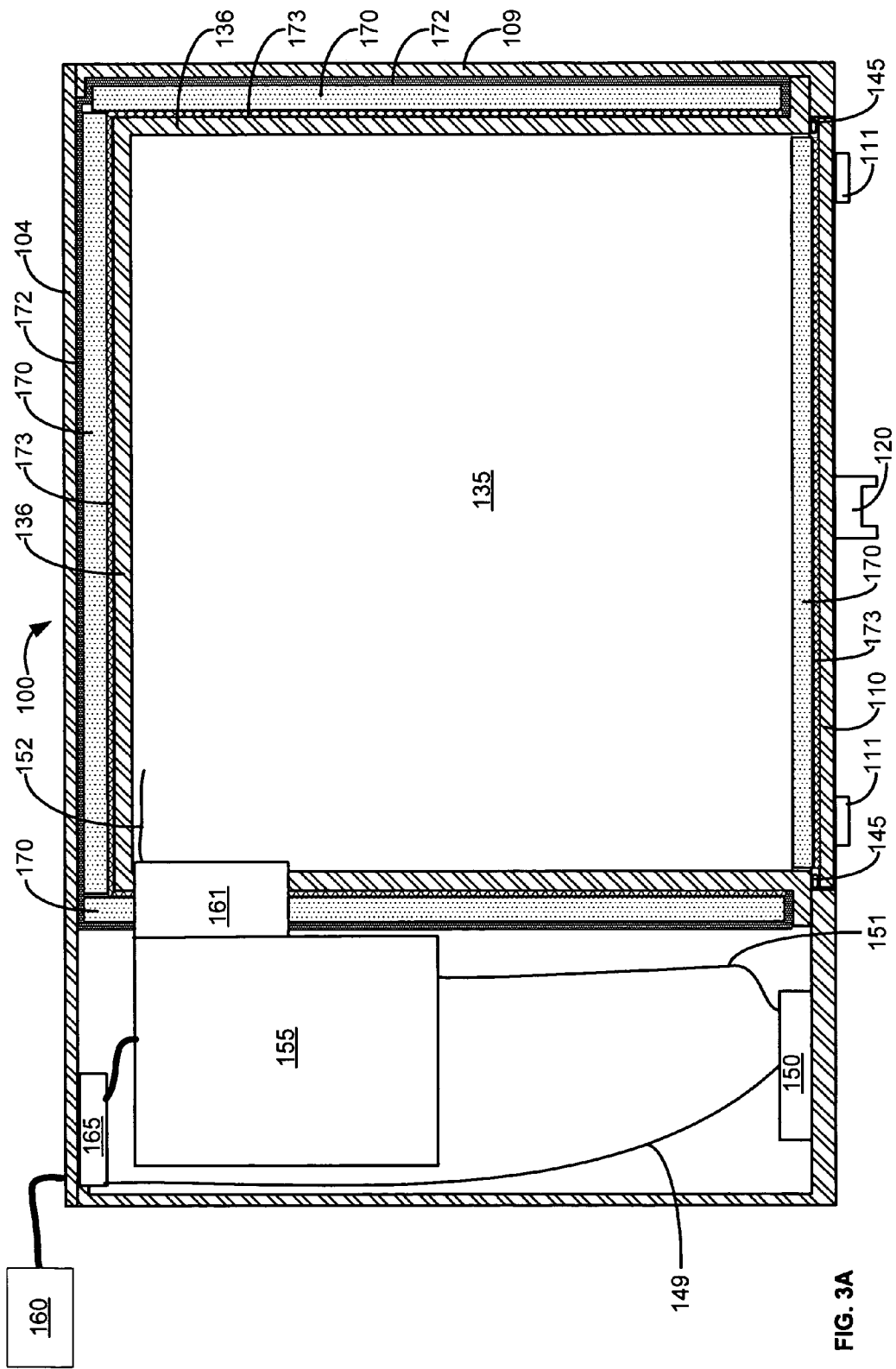
FIG. 3A illustrates a cross-sectional view through the section 3-3 of the potency-preservation apparatus of FIG. 1A.

FIG. 3A is a cross-sectional view through the section 3-3 of FIG. 1A illustrating the interior component arrangements of secure climate-control system 100. Preferably, temperature controller 140 comprises digital thermometer 150, temperature adjuster 155, power supply 160, and power regulator 165, as shown (at least embodying herein temperature controller means for controlling at least one user-definable temperature of said closable compartment means). Preferably, temperature adjuster 155 includes duct 161 to communicate heat or cold from temperature adjuster 155 into closable compartment 135, as shown.

In a preferred embodiment, temperature adjuster 155 may comprise a heat pump. In yet a further preferred embodiment, temperature adjuster 155 may comprise a heater. Upon reading this specification, it will be understood by those of skill in the art that, under appropriate circumstances, such as user preference, advances in technology, etc., other temperature adjusters, such as sterling engines, Peltier junctions, chemical endothermic or exothermic reactions, etc., may suffice. The installation, configuration, and use of various temperature adjusters 155 is well known in the art of conventional refrigeration and heating.

Figure 3B:
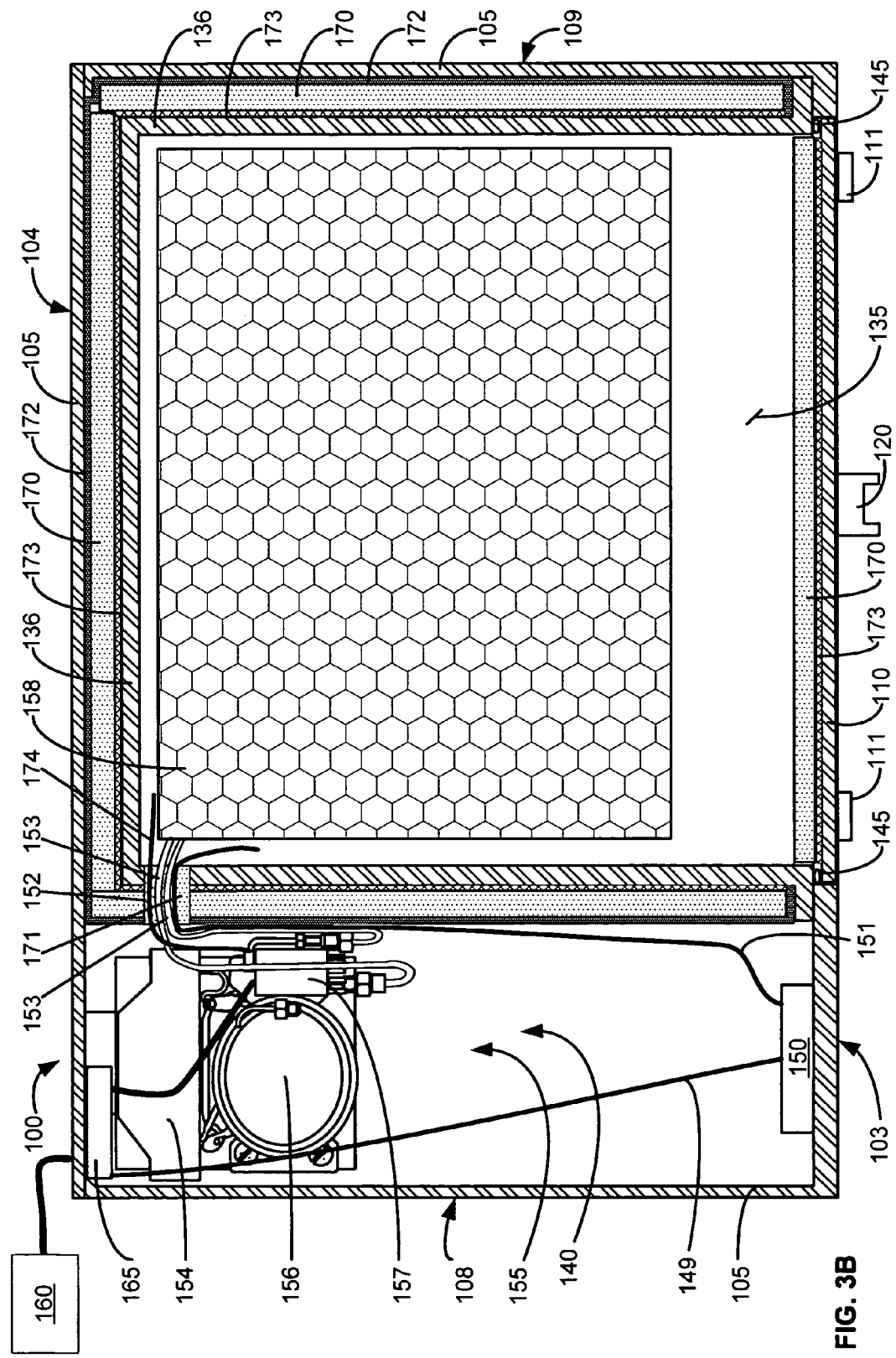
FIG. 3B illustrates a cross-sectional view through the section 3-3 of the potency-preservation apparatus of FIG. 1A.

FIG. 3B is a cross-sectional view through the section 3-3 of FIG. 1A illustrating internal component arrangements of secure climate-control system 100. In the embodiment of FIG. 3B, temperature adjuster 155 preferably comprises a cooler system, preferably a small air conditioning unit having a 12- or 24-volt compressor 156, a condenser 157, and an evaporator 158, as shown (at least embodying herein temperature adjuster means for adjusting at least one temperature of said closable compartment means). Preferably, temperature adjuster 155 has a cooling fan 154, as shown. The source of heat or cold, such as, for example, evaporator 158, is preferably inside closable compartment 135, as shown. Preferably, evaporator 158 is placed near the top of closable compartment 135, with sufficient airspace around condenser 158 to permit airflow, as shown. Preferably, evaporator 158 is held in place with metal spacers 159 (as shown in FIG. 2B). Upon reading this specification, those of skill in the art will understand that, under appropriate circumstances, such as intended use, advances in technology, etc., other evaporators, such as plate evaporators, coil evaporators, box evaporators having a freezer compartment, etc., may suffice.

Power supply 160 is preferably a 12-volt or 24-volt DC electrical power supply, preferably of the sort commonly known in the art, as shown. Preferably, power supply 160 may be an electrical battery, such as, for example, a 12-volt DC battery. Preferably, power supply 160 may be the electrical system of the ERV 101 in which secure climate-controller 100 is installed, as shown. Preferably, power supply 160 may be a shoreline connecting to a land-based electrical grid. Most preferably, power supply 160 is the ERV 101 electrical system, as shown, and power supply 160 draws power from the ERV 101 battery even when the ERV 101 is turned off. This also preferably permits power supply 160 to be fed by the landline to the ERV 101 when the ERV 101 is docked, as is known in the art. Upon reading the teachings of this specification, those with ordinary skill in the art will now understand that, under appropriate circumstances, considering issues such as, intended use, cost, etc., other power arrangements may suffice, such as, for example, the power supply may be a rechargeable battery. Under appropriate circumstances, secure climate-controller 100 may be capable of receiving power from multiple power supplies 160. Upon reading this specification, those of skill in the art will understand that under appropriate circumstances, such as the voltage of the ERV electrical system, user preference, advances in technology, etc., other electrical power sources, such as 120 Volt AC, 42 Volt DC, nonstandard vehicle power arrangements, hydrogen fuel cell, solar power, etc., may suffice.

Preferably, power regulator 165 of temperature adjuster 155 responds to a defined drop in voltage by shutting down temperature adjuster 155 in order to avoid completely draining power source 160. Preferably, power regulator 165 of temperature adjuster 155 responds to a return to an appropriate defined voltage by turning on temperature adjuster 155. This is particularly preferred where power source 160 is an ERV 101 power supply, in order to avoid draining the battery of ERV 101.

Under appropriate circumstances, power regulator 165 may respond to a rapid change in the temperature of the closable compartment 135 by shutting off temperature adjuster 155, in order to conserve power when door 110 is open, and restoring power when door 110 is closed again, as indicated by a stabilization of the temperature in closable compartment 135. Under appropriate circumstances, power regulator 165 may respond to prolonged operation of temperature adjuster 155. Under appropriate circumstances, power regulator 165 may respond to a door position sensor.

Preferably, closable compartment 135 has insulation to help maintain a constant user-selected temperature in closable compartment 135, as shown. Most preferably, closable compartment 135 is insulated with vacuum panels 170, spray foam 171, and plastic cushion wrap 172, as shown. Vacuum insulation panels 170 are preferably ¾-inch-thick membrane-covered vacuum insulation panels, preferably of the sort commonly known in the art, with an insulation R-value of about 30, as shown. Vacuum insulation panels 170 are preferably attached to the outside of the walls 136 of closable compartment 135 on the top, bottom, back, left, and right sides with adhesive 173, as shown. Walls 136 are preferably metal, preferably aluminum, as shown. Because vacuum insulation panels 170 are vulnerable to punctures, plastic cushion wrap 172 is preferably placed between vacuum insulation panels 170 and cover 105 as shown. Plastic cushion wrap 172 also adds some insulation value.

Door 110 is also preferably insulated with a vacuum insulation panel 170, which is preferably attached to door 110 with adhesive 173, as shown.

Spray foam 171 is preferably used to fill conduit 174, as shown. Conduit 174 preferably replaces duct 161 in this embodiment. Preferably, conduit 174 is a hole communicating between the outside and the inside of closable compartment 135 in order to pass gas lines 153, probe 151 of digital thermometer 150, and thermostat probe 152 into closable compartment 135, as shown. Conduit 174 is then preferably sealed with spray foam 171 in order to prevent air leaks, as shown. Upon reading this specification those of skill in the art will understand that, under appropriate circumstances, such as advances in technology, user preference, intended use, etc., other types of insulation, such as fiberglass, spray-in-place foam, rock wool, vacuum-walled compartments, insulating foam panels, fiber insulation, polystyrene, reflective foils, etc., may suffice.

Preferably, evaporator 158 controls humidity in closable compartment 135 by freezing water vapor present in closable compartment 135 onto evaporator 158 in order to maintain a dry environment. Upon reading this specification, those of skill in the art will understand that, under appropriate circumstances, such as advances in technology, user preference, etc., other ways of controlling humidity, such as desiccants, humidifiers, dehumidifiers, drains, etc., may suffice.

Preferably, digital thermometer 150 displays the temperature in closable compartment 135 on the front 103 of secure climate-controller 100 through an opening in cover 105, as shown. Preferably, digital thermometer 150 uses probe 151 through conduit 174 to read the temperature in closable compartment 135, as shown. Digital thermometer 150 is preferably powered by an internal battery, but may be powered by power line 149 connected to power regulator 165, as shown. Most preferably, thermometer 150 is a digital controller of the Universal Infrared Series, manufactured by Carel srl of Padova, Italy, as shown. Preferably, digital thermometer 150 may be directly linked to temperature adjuster 155 and may serve as thermostat 152.

In this preferred embodiment of secure climate-controller 100, the temperature controller 140 is housed on the left side 108 of secure climate-controller 100, as shown. Preferably, temperature controller 140 is located inside cover 105 approximately adjacent to closable compartment 135, as shown. For example, temperature controller 140 may be located to the left, or to the right, or under, or above, or behind, or between, closable compartments 135. Preferably, multiple temperature controllers 140 may be used, particularly where there are multiple closable compartments 135. Preferably, temperature controllers 140 may be installed in any useful orientation in secure climate-controller 100.

Figure 4:
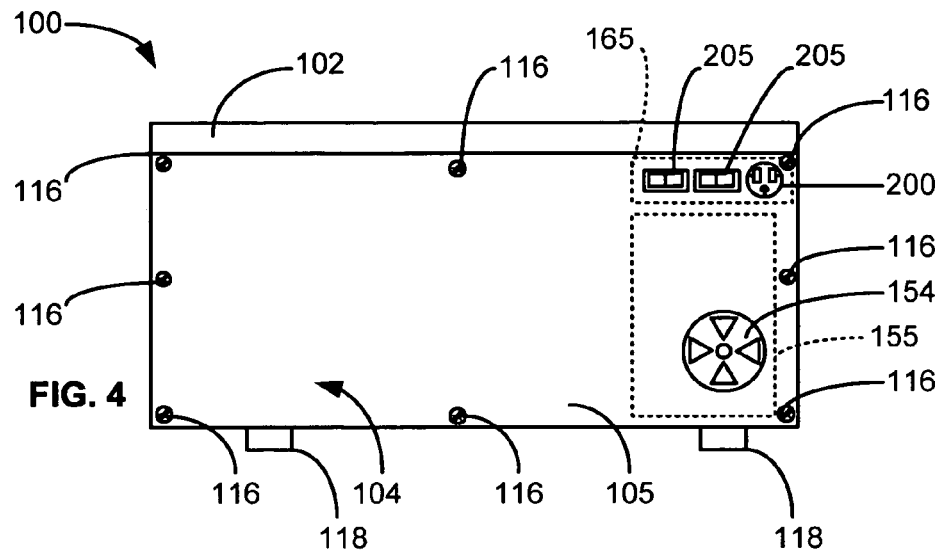
FIG. 4 illustrates a back view of the potency-preservation apparatus of FIG. 1A.

FIG. 4 illustrates a back view of the secure climate-controller of FIG. 1A. Referring to FIG. 4 with continued reference to the prior figures, temperature adjuster 155 preferably comprises a fan 154 to help dissipate excess heat from temperature adjuster 155, as shown. For example, fan 154 may draw in outside air to cool the compressor 157 and condenser 156 of an air conditioning unit, as shown. Preferably, cover 105 is metal, and helps to cool temperature adjuster 155 by acting as a heat sink and/or a cooling fin, as shown. Upon reading this specification, those of ordinary skill in the art will understand that, under appropriate circumstances, such as advances in technology, user preference, intended use, etc., other means of dissipating excess heat or cold from the temperature adjuster, such as water cooling, water heating, other heat sinks, other heat transfer fins, etc., may suffice.

Preferably, power plug 200 and breakers 205, which are part of power regulator 165, are accessible on the back 104 of secure climate-controller 100, as shown. Preferably breakers 205, which may be 2-amp and a 15-amp breakers, disconnect power supply 160 from temperature adjuster 155 when a potentially damaging power surge occurs. Preferably breakers 205 are toggle-type breakers that are easily reset by the user, as shown.

Power plug 200 may be of any type required by the user. Preferably, power plug 200 is a female power plug suitable for receiving a male power plug that is connectable to power supply 160. Power supply 160 is most preferably ERV 101's power supply, allowing secure climate-controller 100 to run on the power supply of ERV 101 whether ERV 101 is running (whereby power is supplied by the ERV alternator), parked (where the ERV power is supplied by the ERV battery), or docked to a landline (where the ERV power is supplied by the landline).

Secure climate-controller 100 is preferably fabricated with permanent connectors, preferably nuts and bolts 116, as shown. Upon reading this specification those of skill in the art will understand that, under appropriate circumstances, such as user preference, materials requirements, economy of manufacture, etc., other fasteners, such as welds, screws, clips, adhesives, etc., may suffice.

Figure 5:
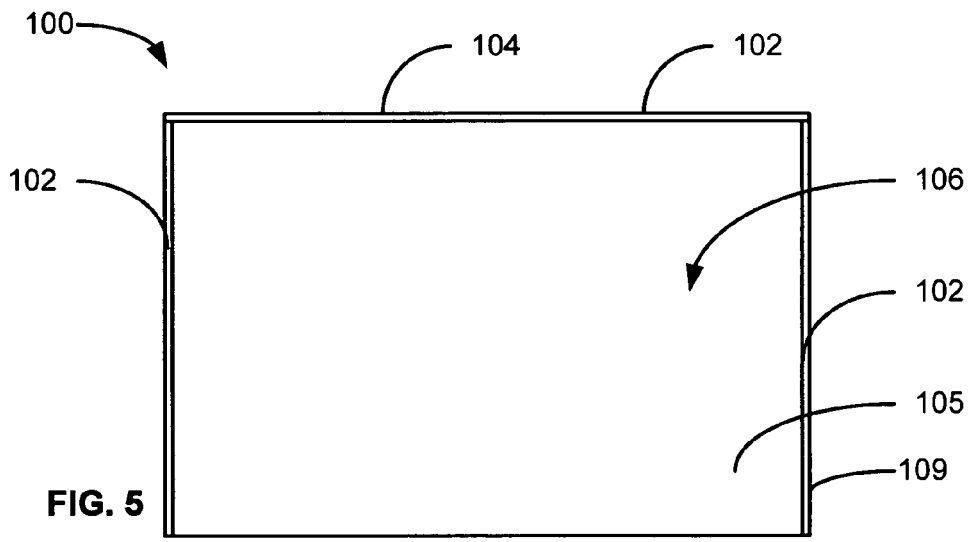
FIG. 5 illustrates a top view of the potency-preservation apparatus of FIG. 1A.

FIG. 5 illustrates a top view of the secure climate-controller of FIG. 1A. Preferably, cover 105 is metal, preferably aluminum, preferably 12-gauge aluminum, most preferably polished 12-gauge diamond plate aluminum of the type commonly used on fire engines, as shown. Upon reading this specification, those of skill in the art will understand that, under appropriate circumstances, such as user preference, advances in technology, aesthetic reasons, etc., other materials, such as steel, other metals, plastics, wood, laminates, etc., may suffice for the cover.

Preferably, one or more flanges 102 are built up on the top 106 of cover 105 to form a useful storage tray for holding items, as shown. Upon reading this specification, those of skill in the art will understand that, under appropriate circumstances, such as user preference, advances in technology, aesthetic reasons, point of installation, etc., other shapes for the top of cover portions, such as sloped, flat, rounded, etc., may suffice. Under appropriate circumstances, secure climate-controller 100 may be installed in a wall of a vehicle, wherein the top 106, bottom 107 (see FIG. 6), left side 108, right side 109 and back 104 of cover 105 may be absent.

Figure 6:
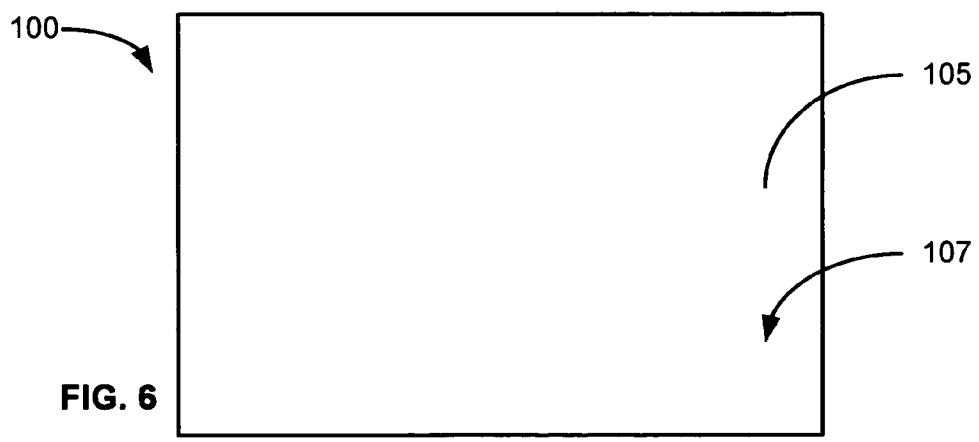
FIG. 6 illustrates a bottom view of the potency-preservation apparatus of FIG. 1A.

FIG. 6 illustrates a bottom view of the secure climate-controller of FIG. 1A. Preferably, the bottom 107 of cover 105 is made of the same material as the rest of cover 107, as shown. Upon reading this specification, those of skill in the art will understand that, under appropriate circumstances, such as user preference, advances in technology, aesthetic reasons, point of installation, etc., the bottom of cover portions may be made of different materials that the rest of cover 105. Under appropriate circumstances, bottom 107 may be absent and/or may have feet attached.

Figure 7:
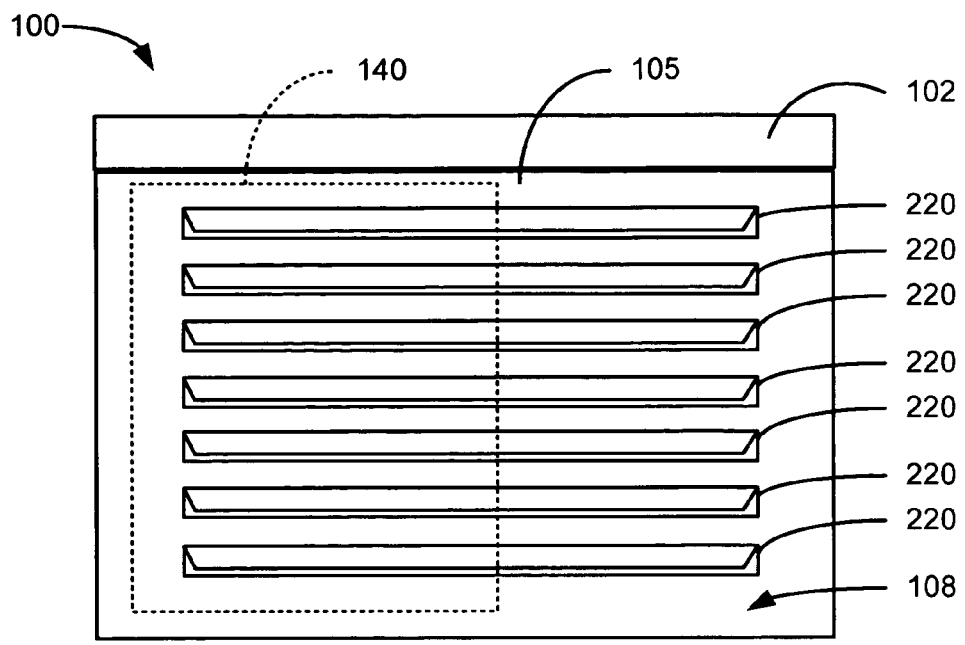
FIG. 7 illustrates a left side view of the potency-preservation apparatus of FIG. 1A.

FIG. 7 illustrates a left side view of the secure climate-controller of FIG. 1A. Preferably, vents 220 permit air to escape from inside of cover 105 in order to assist heat exchange of the air with temperature controller 140, as shown. Preferably, vents 220 are located at least near temperature controller 140, which is on the left side 108 of secure climate-controller 100 in this embodiment, as shown.

Figure 8:
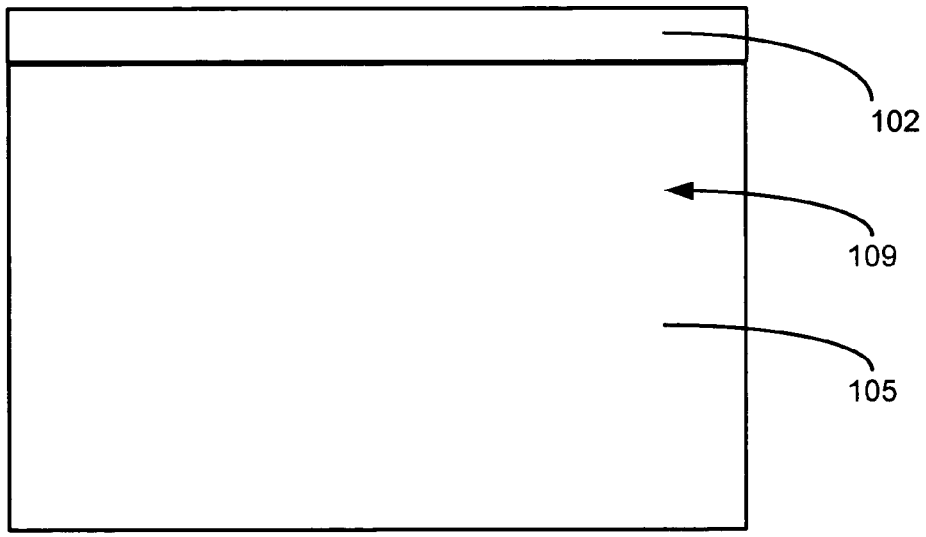
FIG. 8 illustrates a right side view of the potency-preservation apparatus of FIG. 1A.

FIG. 8 illustrates a right side view of the secure climate-control system of FIG. 1A. Preferably, the right side 109 of cover 105 does not have vents 220, unless temperature controller 104 is adjacent, as shown.

Figure 9:
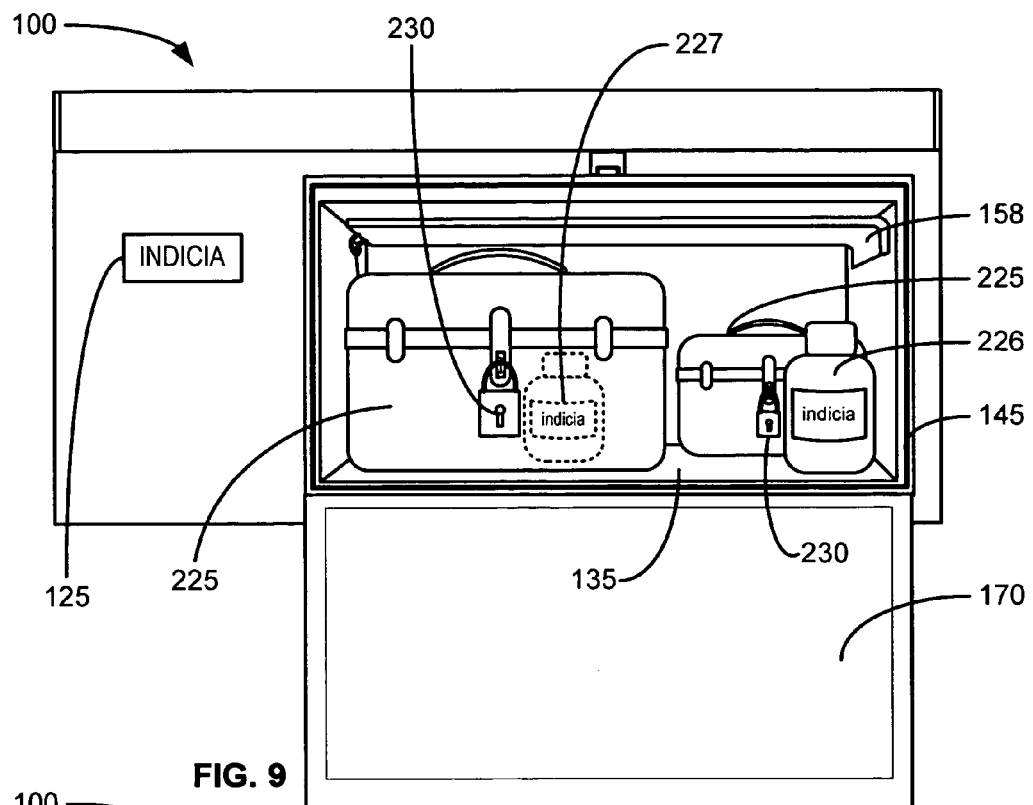
FIG. 9 illustrates a front view of the potency-preservation apparatus of FIG. 1A with multiple storage containers inserted.

FIG. 9 illustrates a front view of the secure climate-control system of FIG. 1A with multiple storage containers 225 inserted. Preferably, storage container 225 permits medical supplies contained in storage container 225 to be quickly transported to the patient after the ERV 101 has arrived at the scene of the emergency. Preferably, multiple storage containers 225 may be used, and may be designated to contain different types of items, as shown. For example, one storage container 225 may be designated to contain drugs while a second storage container 225 may be designated to hold toxicology samples gathered from a patient. Preferably, medical supplies 226 may also be stored directly in compartment 135, as shown.

Container 225 preferably has a lock 230, as shown. Lock 230 may use the same key 122 as lock 115, but preferably uses a different key, combination, or other locking means than lock 115. Preferably, locked containers 225 may be used to hold controlled substances such as, for example, morphine 227, as shown (at least embodying herein container means for containing medical supplies, wherein said container means is adapted to be inserted into said closable compartment means). This provides a double-locking system required by law in many jurisdictions for the control of controlled substances or criminal evidence. Preferably, where the law permits single-lock security for controlled substances, controlled substances may be stored directly in compartment 135, as shown (at least embodying herein closable compartment means for enclosing at least one controlled substance). Preferably, container 225 is not locked if it only contains non-controlled substances, in order to facilitate access in emergencies, as shown.

Figure 10:
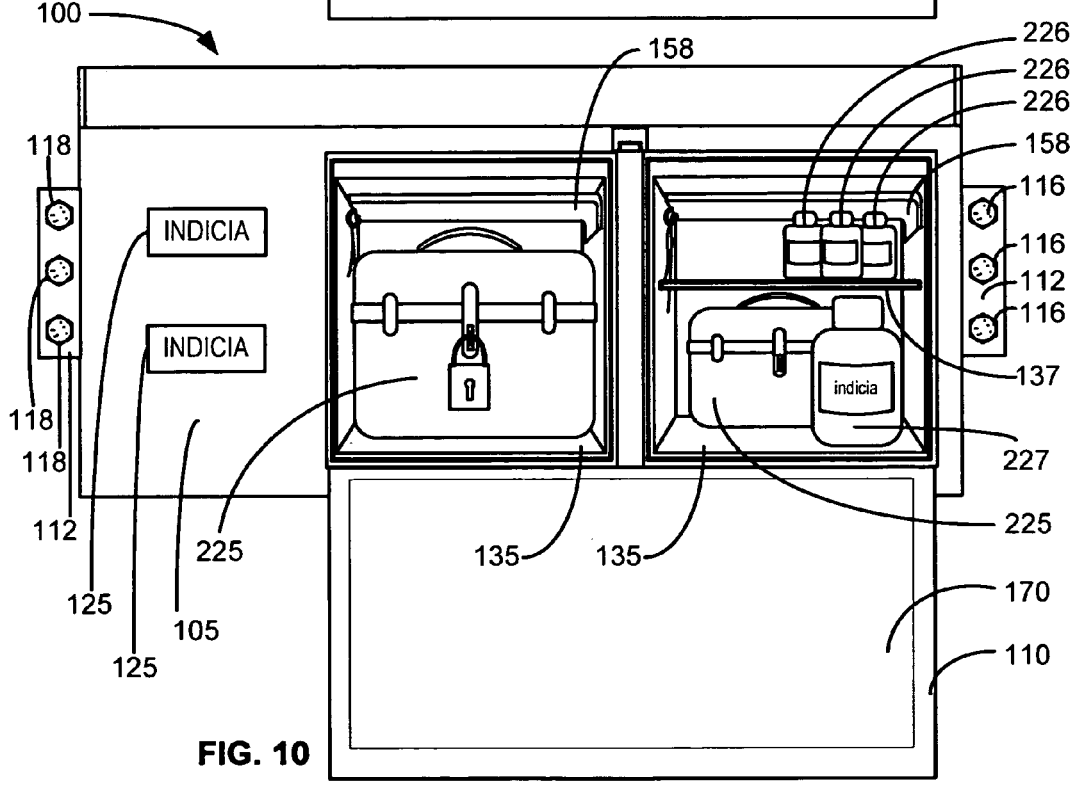
FIG. 10 illustrates a front view of a potency-preservation apparatus according to a preferred embodiment of the present invention, with multiple compartments behind one door.

FIG. 10 illustrates a front view of a secure climate-control system with multiple closable compartments 135 behind one door 110. Preferably, closable compartments 135 may be uniformly temperature controlled, or may each be individually temperature controlled, by one or more temperature controllers 140 or temperature adjusters 155, in any useful combination, as shown. Preferably, closable compartment 135 may contain one or more containers 225, as shown. Preferably, closable compartments 135 may have shelves 137, as shown. Under appropriate circumstances, a closable compartment 135 may have its own additional door, which may be lockable.

Installation flanges 112 are preferably used for installing secure climate-controller 100 in ERV 101. Preferably, permanent connectors 118 are provided with secure climate-controller 100. Preferably, permanent connectors 118 comprise nuts and bolts 116, screws, nails, or other fasteners which pass through one or more holes in installation flanges 112 and firmly attach to a ERV, as shown. Under appropriate circumstances, permanent connectors 118 comprise adhesives, welds, clips, or other attachments. Preferably, installation flanges 112 may be placed as needed on secure climate-controller 100, and are preferably welded to cover 105, as shown. Preferably, secure climate-controller 100 may also be attached to ERV 101 by fastening through any point on cover 105, or closable compartment 135, as needed.

Figure 11:
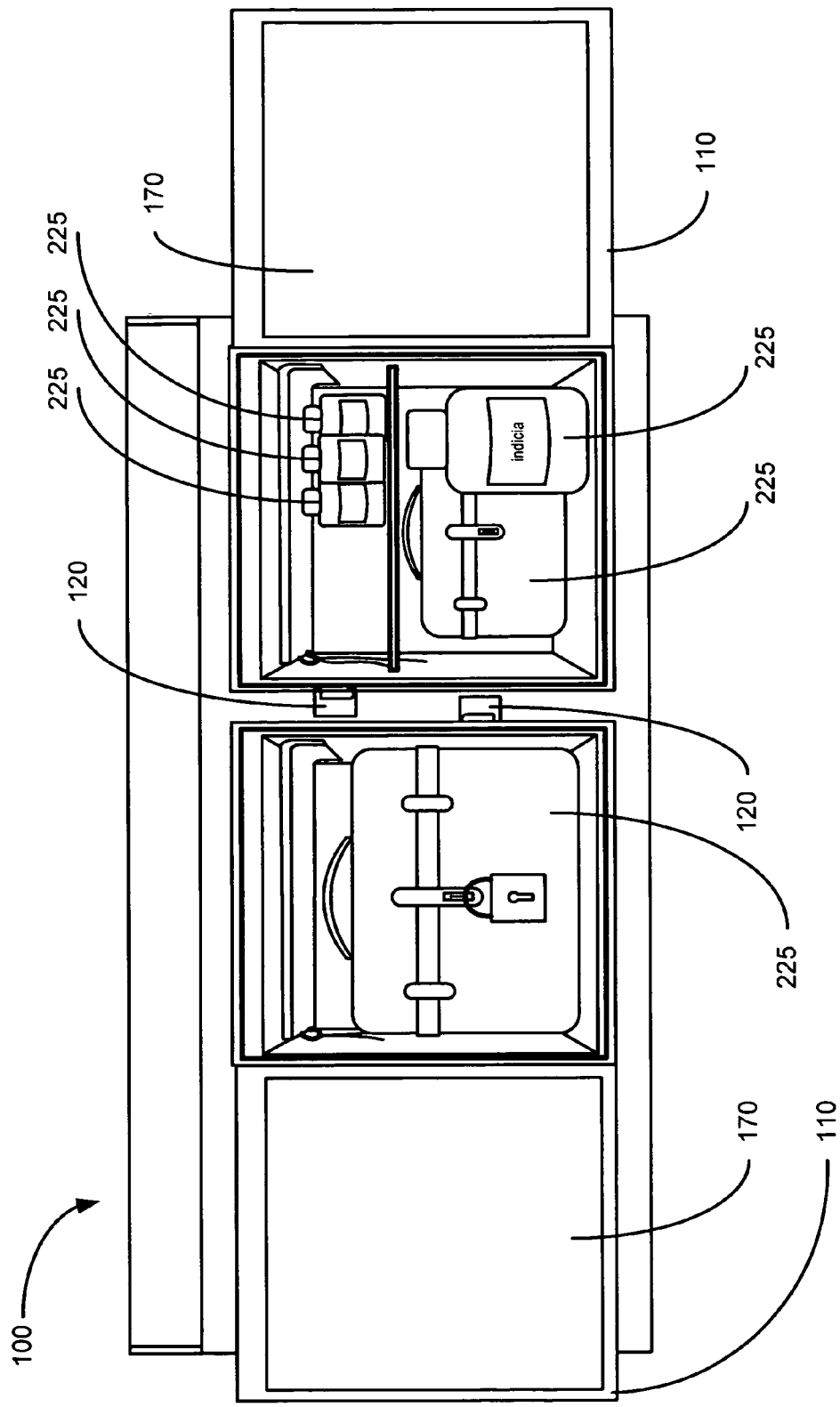
FIG. 11 illustrates a front view of a secure climate-control system according to a preferred embodiment of the present invention, with multiple compartments behind multiple doors.

FIG. 11 illustrates a perspective view of a secure climate-control system with multiple closable compartments 135 behind multiple doors 110. Preferably, doors 110 may have latches 120, which may or may not use the same key or combination, as shown. Preferably, closable compartments 135 may each contain one or more containers 225, as shown. In this preferred embodiment, doors 110 open outward to the left and right, as shown.

Figure 12:
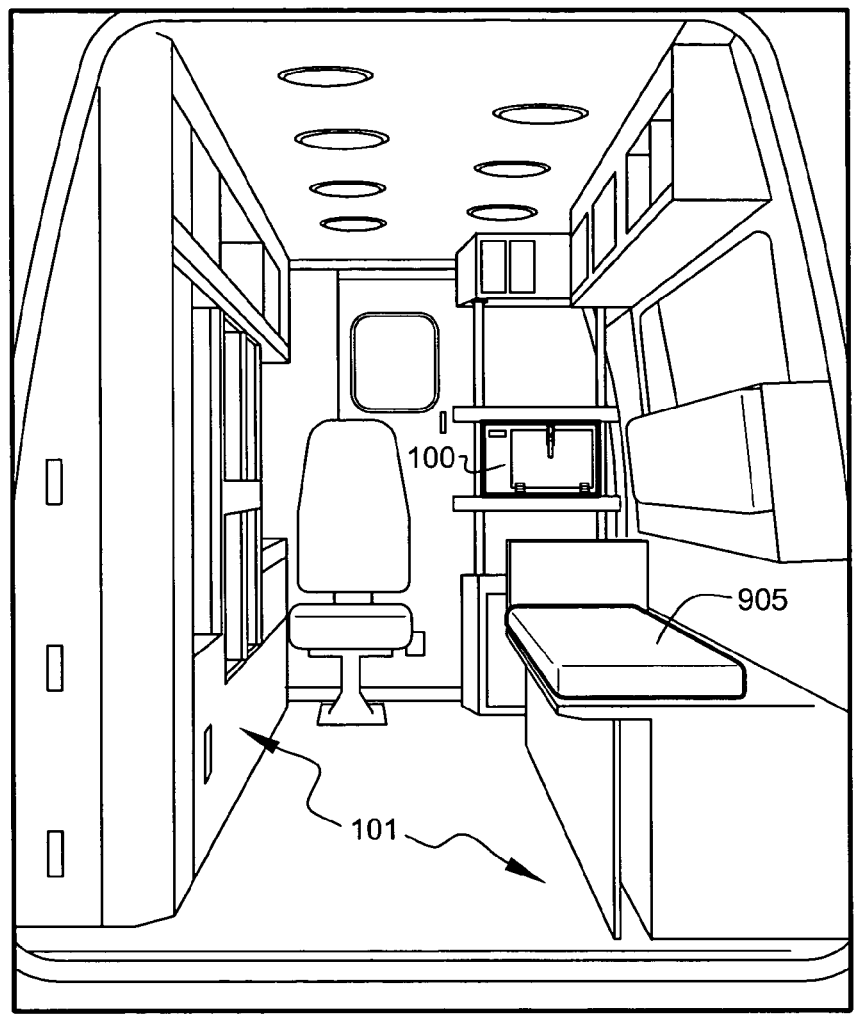
FIG. 12 illustrates a back view of a secure climate-control system according to a preferred embodiment of the present invention.

FIG. 12 illustrates a front view of a secure climate-controller 100 permanently installed within emergency response vehicle 101, together comprising secure climate-control system 900. Referring to FIG. 12 with continued reference to the prior figures, secure climate-controller 100 may be installed in any convenient space on ERV 101, such as, for example, on the floor, in the wall, on the wall, on the exterior, in a cabinet, in the crew cabin, etc. In this preferred embodiment, secure climate-controller 100 is installed in the wall behind the patient cot 905, as shown. The placement will preferably vary with the type, model, and equipment of the particular ERV 101. Preferably, secure climate-controller 100 is installed with an accessible space around it to facilitate airflow to fan 154, and so that plug 200 and breakers 205 are accessible, as shown. Where that is not convenient, ductwork may preferably be used to connect the intake of fan 154, and/or the output of vents 220, with a free-flowing air supply, such as the outside of the vehicle. Also, plug 200, breakers 205, fan 154, and vents 220 may preferably be placed in any conveniently accessible location on secure climate-controller 100, such as on the front 103. Secure climate-controller 100 is preferably permanently installed on ERV 101 with permanent connectors 118, as shown (at least embodying herein permanent connection means for permanently connecting said secure potency-preserving means onto wheeled emergency-response transport means).

The unique nature of secure climate-controller 100, and the special nature of ERVs 101, provide for novel methods of doing business comprising selling and using secure climate-controllers 100 and secure climate-control systems 900, which are preferably custom-made.

Figure 13:
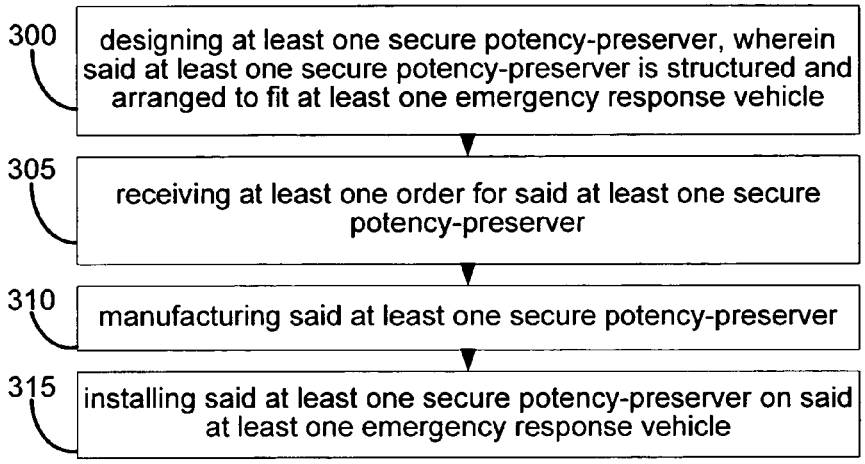
FIG. 13 illustrates a diagram of business method steps according to a preferred embodiment of the present invention.

FIG. 13 illustrates a block diagram of a method of doing business 950, preferably comprising the steps of: designing 300 at least one secure climate-controller 100, wherein said at least one custom secure climate-controller 100 is structured and arranged to fit at least one emergency response vehicle 101; receiving 305 at least one order for said at least one secure climate-controller; manufacturing 310 said at least one secure climate-controller; and installing 315 said at least one secure climate-controller 100 on said at least one emergency response vehicle 101, thereby forming secure climate-control system 900, as shown (at least embodying herein a method of doing business comprising the steps of: designing at least one secure potency-preserver, wherein said at least one secure potency-preserver is structured and arranged to be connected on at least one type of emergency-response vehicle in at least one specified location; receiving at least one order for said at least one secure potency-preserver; manufacturing said at least one secure potency-preserver; and installing said at least one secure potency-preserver on said at least one emergency-response vehicle).

Figure 14:
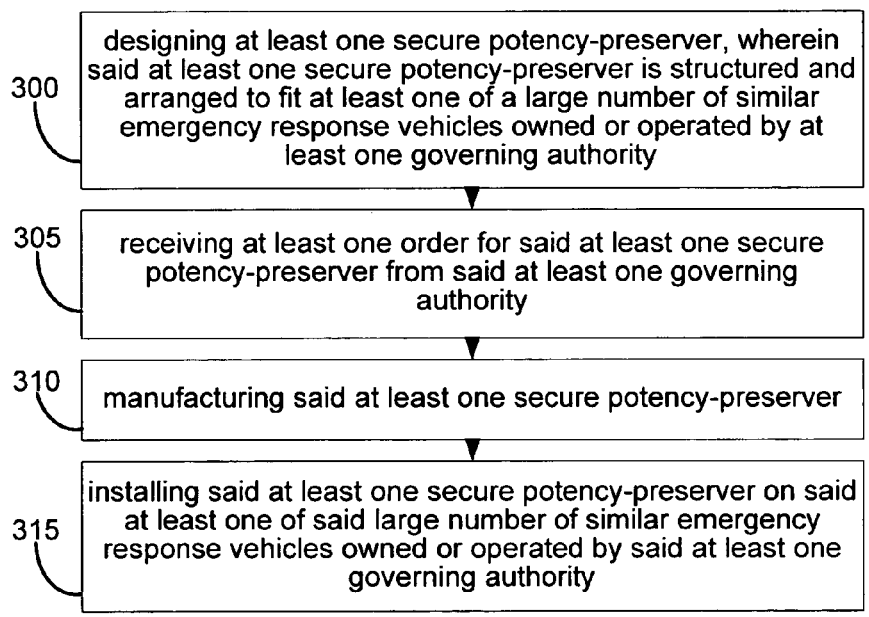
FIG. 14 illustrates a diagram of business method steps according to a preferred embodiment of the present invention.

FIG. 14 illustrates a block diagram of a method of doing business 951, preferably comprising the steps of: designing 300 at least one secure climate-controller 100, wherein said at least one secure climate-controller 100 is structured and arranged to fit at least one of a large number of similar emergency response vehicles 101 owned or operated by a governing authority; receiving 305 an order for at least one secure climate-controller 100 from the governing authority; manufacturing 310 said at least one secure climate-controller 100; and installing 315 at least one secure climate-controller 100 on at least one of the large number of similar emergency response vehicles 101 owned or operated by the governing authority (at least embodying herein a method of doing business comprising the steps of: designing at least one secure potency-preserver, wherein said at least one secure potency-preserver is structured and arranged to fit at least one of a large number of similar emergency response vehicles owned or operated by at least one governing authority; receiving at least one order for said at least one secure potency-preserver from said at least one governing authority; manufacturing said at least one secure potency-preserver; and installing said at least one secure potency-preserver on said at least one of said large number of similar emergency response vehicles owned or operated by said at least one governing authority).

Preferably, designs for such custom installations are made for a large number of similar ERVs owned or operated by at least one governing authority. Thus, that design, although custom for the particular type of ERV and the authority's preferences, is useful in designing and installing such large number of secure climate-controllers 100 of the present invention.

Figure 15:
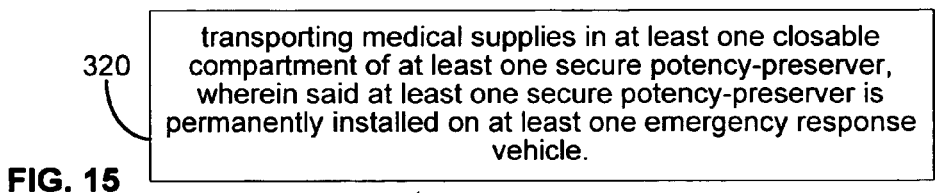
FIG. 15 illustrates a diagram of a business method step according to a preferred embodiment of the present invention.

FIG. 15 illustrates a block diagram of a method of doing business 952, preferably comprising the step of transporting 320 medical supplies in at least one closable compartment 135 of at least one secure climate-controller 100, wherein said at least one secure climate-controller 100 is permanently installed on at least one emergency response vehicle 101 (at least embodying herein a method of doing business comprising the step of transporting medical supplies in at least one closable compartment of at least one secure potency-preserver, wherein said at least one secure potency-preserver is permanently installed on at least one emergency response vehicle).

Figure 16:
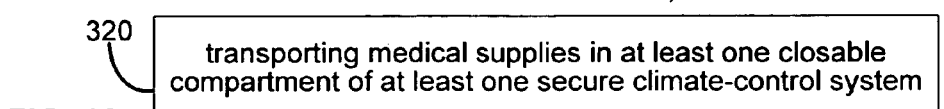
FIG. 16 illustrates a diagram of a business method step according to a preferred embodiment of the present invention.

FIG. 16 illustrates a block diagram of a method of doing business 953, preferably comprising the step of transporting 320 medical supplies in a closable compartment 135 of a secure climate-control system 900, wherein such closable compartment is secured by at least one authentication system comprising at least one user-identification system, as shown (at least embodying herein a method of doing business comprising the step of: transporting medical supplies in at least one closable compartment of at least one climate-control system; wherein such closable compartment is secured by at least one authentication system comprising at least one user-identification system).

These novel business methods permit emergency medical personnel to securely and safely transport a wider array of life-saving medicines and supplies to local emergency medical situations than is conventionally possible.

FIG. 17 illustrates a front view of secure climate-controller 100 according to another preferred embodiment of the present invention. In the preferred embodiment of FIG. 17, secure climate-controller 100 incorporates a sophisticated electronic access control system, as shown. Preferably, access control system 400 (at least embodying herein at least one latch controller) comprises an electronic lock system adapted to interface with electrically-actuated latch 402 located at door 110, as shown. Preferably, lock control system 400 comprises internal lock-controlling electronics having a non-volatile memory component (at least embodying herein at least one data memory) adapted to store user codes, supervisor codes, and audit trails. Preferably, lock control system 400 is optionally programmable using proprietary software. Alternately, lock control system 400 can be programmed manually by presenting a supervisor's credential.

Preferably, the software program creates a database of users and lock control systems 400 on a host computer. Typically, each user in the host computer's database is given a unique identifier that is downloaded to the internal memory of each lock control system 400 to which the user has access. Preferably, the internal memory of lock control system 400 is divided into multiple "data slots" that store user identifier data. Preferably, each lock control system 400 comprises an internal memory capable of storing at least about 250 user identifiers. Preferably, the host computer containing the software program has the ability to connect to lock control system 400 and update the internal memory to correspond with its own database. Preferably, the host computer containing the software program has the ability to connect to lock control system 400 using standard data connection and transfer protocols. For example, the host computer may be preferably adapted to transfer data to and from lock control system 400 using a physical data transfer method, such as, by means of a data transfer cable. In addition, the host computer may be preferably adapted to transfer data to and from lock control system 400 using a wireless connection, such as, for example, using radio signals, infrared transfers, etc. Upon reading the teachings of this specification, those with ordinary skill in the art will now understand that, under appropriate circumstances, considering issues such as, vehicle service areas, operational requirements, etc., the use of specific wireless data transfer arrangements, such as wireless LANs, Wi-Fi, mobile data networking, Bluetooth® wireless networking, various forms of 082.11x standards, newly developed/adopted wireless data transmission standards etc., may suffice.

Preferably, the software program also has the ability to gather and manipulate the audit trail, or past operation log, of lock control system 400. Preferably, audit trail information contains the unique name or number assigned to lock control system 400, the name of the user attempting to gain access, the credential used, whether access was granted or denied, and the date and time of each interaction. Upon reading this specification, those of ordinary skill in the art will understand that, under appropriate circumstances, considering such issues as regulatory requirements, intended use, etc., other auditing and data tracking functions, such as, recording the temperature in the closable compartment over time (in order to provide proof that temperature-sensitive substances have been maintained at the correct temperature in storage), etc., may suffice.

Preferably, the software program has the ability to manipulate the "data slots" within lock control system 400 using an external data port on lock control system 400 and at least one portable data transfer device (at least embodying herein at least one data port adapted to permit external access to such stored authentication data). Preferably, the software program is adapted to initialize the portable data transfer device to retrieve an audit trail of lock control system 400, to update the system's internal database of users (to match the host computer's database), or to update the real time clock within lock control system 400.

In the embodiment of FIG. 17, lock control system 400 (at least embodying herein wherein such at least one latch controller comprises at least one electronic device structured and arranged to control at least one locking function of such at least one electrically-actuated latch) comprises numeric keypad 404, as shown. Preferably, numeric keypad 404 permits a user to access secure climate-controller 100 by entering a user identifier, in this case a Personal Identification Number (PIN code). Preferably, lock control system 400 is adapted to release electrically-actuated latch 402 on authenticating the PIN code using the internally-stored user data (at least embodying herein wherein such at least one electronic device is structured and arrange to control such at least one locking function on receiving at least one electronic authentication and at least embodying herein wherein such at least one electronic device performs such at least one electronic authentication by receiving at least one authenticating key code from at least one keypad). On releasing electrically-actuated latch 402, door 110 may be swung away to permit access to the interior compartments.

FIG. 18 illustrates a front view of card swipe lock 406 used to control access to secure climate-controller 100 according to another preferred embodiment of the present invention. Card swipe lock 406 comprises a preferred alternate embodiment of lock control system 400. Preferably, card swipe lock 406 is adapted to receive user identifier data from magnetic stripe card 410, a common credit-type card, as shown. Preferably, card swipe lock 406 comprises a magnetic stripe reader located along card slot 408, as shown. Preferably, a user accesses secure climate-controller 100 by passing magnetic stripe card 410 containing user identifier data through slot 408. Preferably, card swipe lock 406 is adapted to release electrically-actuated latch 402 on authenticating the user identifier data retrieved by the magnetic stripe reader (at least embodying herein wherein such at least one electronic device is structured and arrange to control such at least one locking function on receiving at least one electronic authentication). Upon reading the teachings of this specification, those with ordinary skill in the art will now understand that, under appropriate circumstances, considering issues such as intended use, user preference, etc., the use of other magnetic stripe card arrangements such as, for example, using a magnetic stripe card to program lock control systems, etc., may suffice.

FIG. 19 illustrates a front view of digital touch-key lock 412 used to control access to secure climate-controller 100 according to a preferred embodiment of the present invention. Digital touch-key lock 412 comprises another preferred embodiment of lock control system 400. Preferably, digital touch-key lock 412 is adapted to operate when the user touches digital touch-key 414 to receptacle 416. Preferably, digital touch-key lock 412 is adapted to release electrically-actuated latch 402 on authenticating the user identifier data retrieved from digital touch-key 414 (at least embodying herein wherein such at least one electronic device is structured and arrange to control such at least one locking function on receiving at least one electronic authentication and at least embodying herein wherein such at least one electronic device performs such at least one electronic authentication by acquiring authentication data from at least one data-containing device). As previously described, digital touch-key 414 is also adapted to transfer programming data, audit trail data, etc., to and from lock control system 400.

FIG. 20 illustrates a front view of proximity card lock 418 used to control access to secure climate-controller 100 according to a preferred embodiment of the present invention. Proximity card lock 418 comprises yet another preferred embodiment of lock control system 400. Preferably, proximity card lock 418 is adapted to permit the transfer of user identifier data when a user physically moves proximity card 420 near proximity card lock 418. Preferably, proximity card lock 418 is adapted to utilize standard HID proximity cards, as shown. Preferably, proximity card lock 418 is adapted to release electrically-actuated latch 402 on authenticating the user identifier data retrieved from proximity card 420 (at least embodying herein wherein such at least one electronic device is structured and arrange to control such at least one locking function on receiving at least one electronic authentication and at least embodying herein wherein such at least one data-containing device is adapted to provide such at least one electronic authentication by wireless means).

Preferably, lock control system 400 of FIG. 17 through FIG. 20 is similar in specification to systems commercially available from CompX International of River Grove, Ill. (www.compxnet.com).

FIG. 21 illustrates a front view of biometrically keyed lock 322 used to access secure climate-controller 100 according to a preferred embodiment of the present invention. Biometrically keyed lock 422 comprises yet another preferred embodiment of lock control system 400. Preferably, biometrically keyed lock 422 is adapted to read biometric information from a user and to use such data to authenticate the user's identification and ability to access secure climate-controller 100. Preferably, biometrically keyed lock 422 utilizes common biometric identifiers, such as voice pattern recognition, iris/retina scanning, or fingerprint scans, as shown. For example, to access secure climate-controller 100, an authorized user may press a finger or thumb against print scanner 424. Preferably, print scanner 424 converts the fingerprint patterns of the user to identifier data that can be compared against stored data within biometrically keyed lock 422. Preferably, biometrically keyed lock 422 is adapted to release electrically-actuated latch 402 on authenticating the user identifier data retrieved from print scanner 424 (at least embodying herein wherein such at least one electronic device is structured and arrange to control such at least one locking function on receiving at least one electronic authentication and at least embodying herein wherein such at least one electronic device performs such at least one electronic authentication by analyzing at least one biometric identifier). Upon reading the teachings of this specification, those with ordinary skill in the art will now understand that, under appropriate circumstances, considering issues such as advances in technology, level of required security, etc., other biometric identification arrangements such as, for example, the use of vein pattern scanning, key stroke rhythm, face recognition, immediate DNA marker analysis, etc., may suffice.

Furthermore, those with ordinary skill in the art, upon reading the teachings of this specification, will now understand that, under appropriate circumstances, considering issues such as regulatory requirements, required security, etc., other electronic lock control system arrangements such as, for example, combining (for enhanced security) a numeric keypad with a card swipe, or other such combinations, etc., may suffice.

Figure 22:
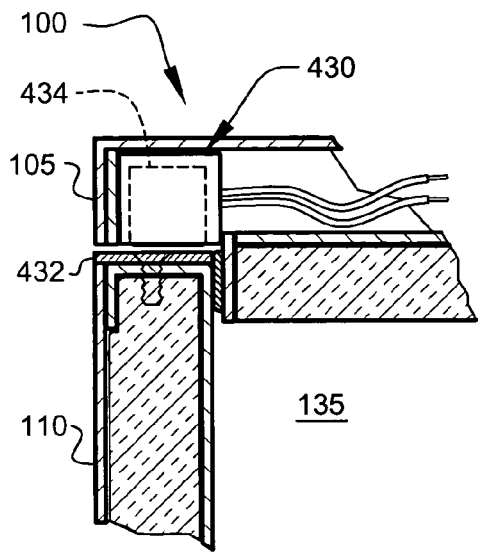
FIG. 22 illustrates a magnetic shear lock used to access the secure climate-controller according to a preferred embodiment of the present invention.

FIG. 22 illustrates magnetic shear lock 430 used to control access of secure climate-controller 100 according to a preferred embodiment of the present invention. Magnetic shear lock 430 comprises a preferred embodiment of electrically-actuated latch 402 shown in FIG. 17. Preferably, magnetic shear lock 430 is adapted to operate with lock control system 400. Preferably, magnetic shear lock 430 comprises strike plate 432 and electromagnet assembly 434, as shown. Preferably, magnetic shear lock 430 is firmly fixed within cover 105, as shown. Preferably, strike plate 432 is mounted to door 110, as shown. Preferably, electromagnet assembly 434, when electrically energized, magnetically retains strike plate 432/door 110 in a fixed closed position, as shown. Preferably, release of door 110 is achieved by switching off power to electromagnet assembly 434. Preferably, magnetic shear lock 330 is powered by power supply 160 (see FIG. 3B) and controlled by lock control system 300 or similar controller. Preferably, magnetic shear lock 430 comprises a device similar in specification to commercially available units produced by Securitron Magnalock Corp. of Sparks, Nev., USA.

Figure 23:
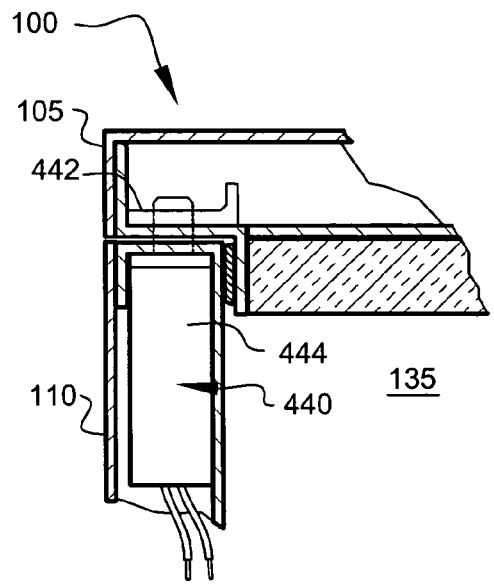
FIG. 23 illustrates an electrically-actuated throw lock used to control access to the secure climate-controller according to a preferred embodiment of the present invention.

FIG. 23 illustrates electrically-actuated throw lock 440 used to control access of secure climate-controller 100 according to a preferred embodiment of the present invention. Preferably, electrically-actuated throw lock 440 comprises a solenoid and/or motor-driven electric throw bolt, as shown. Preferably, electrically-actuated throw lock 440 comprises strike plate 442 and electrically operated bolt assembly 444, as shown. Preferably, strike plate 442 is firmly fixed within cover 105, as shown. Preferably, electrically operated bolt assembly 444 is mounted within door 110, as shown. Preferably, electrically-actuated throw lock 440, when actuated, retains door 110 in a fixed closed position, as shown. Preferably, electrically-actuated throw lock 440 is powered by power supply 160 (see FIG. 3B) and controlled by lock control system 400 or a similar controller. Preferably, electrically-actuated throw lock 440 comprises a device similar in specification to commercially available units produced by Security Door Controls of Westlake Village, Calif., USA.

Figure 24:
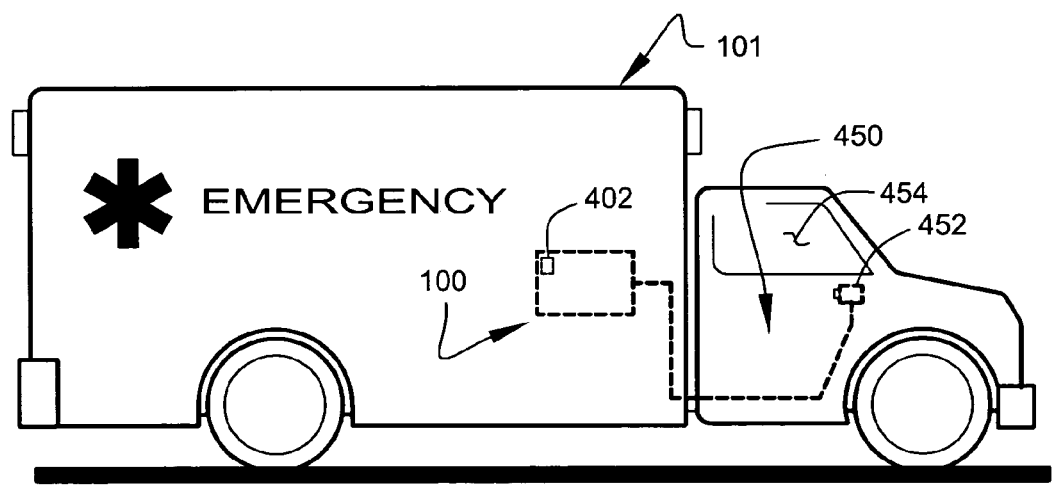
FIG. 24 illustrates a remotely located lock release according to a preferred embodiment of the present invention.

FIG. 24 illustrates remotely located lock release 450 according to a preferred embodiment of the present invention. In the embodiment of FIG. 24 electrically-actuated latch 402 is actuated using remote electrical switch 452, as shown (at least embodying herein at least one electric switch adapted to actuate such at least one electrically-actuated latch). Preferably, remotely located lock release 450 is located within a secured area of ERV 101, such as interior cab 454, as shown (at least embodying herein a first portion of the at least one wheeled emergency-response transport). Preferably, remote electrical switch 452 comprises a keyed electrical switch. However, upon reading the teachings of this specification, those with ordinary skill in the art will now understand that, under appropriate circumstances, considering issues such as security requirements, prevailing regulations, etc., other switching arrangements such as, for example, the use of remotely located electronic systems similar to the other lock control systems described herein, may suffice. Preferably, remote electrical switch 452 is electrically coupled with electrically-actuated latch 402 by means of electrical conductor 456, as shown. Upon reading the teachings of this specification, those with ordinary skill in the art will now understand that, under appropriate circumstances, considering issues such as vehicle type, system requirements, etc., other arrangements such as, for example, the use of a wireless link between the electrically-actuated latch and a remote electrical switch, etc., may suffice.

Although applicant has described applicant's preferred embodiments of this invention, it will be understood that the broadest scope of this invention includes such modifications as diverse shapes and sizes and materials. Such scope is limited only by the below claims as read in connection with the above specification.

Further, many other advantages of applicant's invention will be apparent to those skilled in the art from the above descriptions and the below claims.

What is claimed is:

1. A secure climate-control system, for preserving potency of at least one controlled substance on at least one wheeled emergency-response transport, comprising:

a) at least one secure potency-preserver structured and arranged to securely preserve potency of such at least one controlled substance; and
b) at least one permanent connector adapted to permanently connect said at least one secure potency-preserver onto the at least one wheeled emergency-response transport.

2. The secure climate-control system, according to claim 1 wherein said at least one secure potency-preserver comprises:

a) at least one closable compartment adapted to enclose at least one controlled substance;
b) wherein said at least one closable compartment comprises at least one openable access;
c) at least one temperature controller adapted to control at least one user-definable temperature of said at least one closable compartment;
d) at least one lock to lock said at least one openable access in a closed position to prevent unauthorized access to said at least one closable compartment.

3. The secure climate-control system, according to claim 2 further comprising at least one wheeled emergency-response transport adapted to land-transport emergency-response personnel and controlled substances to emergency situations.

4. The secure climate-control system, according to claim 2, wherein said at least one temperature controller comprises at least one temperature indicator structured and arranged to indicate at least one temperature of said at least one closable compartment.

5. The secure climate-control system, according to claim 4 wherein said at least one temperature indicator comprises at least one thermometer.

6. The secure climate-control system according to claim 2 wherein said at least one temperature controller comprises at least one thermostat.

7. The secure climate-control system, according to claim 2 wherein said at least one temperature controller comprises at least one temperature adjuster structured and arranged to adjust at least one temperature of said at least one closable compartment.

8. The secure climate-control system, according to claim 7 further comprising at least one heat sink structured and arranged to dissipate excess heat.

9. The secure climate-control system, according to claim 7 further comprising at least one vent structured and arranged to dissipate excess heat.

10. The secure climate-control system, according to claim 7 further comprising at least one fan structured and arranged to dissipate excess heat.

11. The secure climate-control system, according to claim 2 further comprising at least one humidity controller structured and arranged to control at least one humidity level in said at least one closable compartment.

12. The secure climate-control system, according to claim 2 further comprising at least one insulator structured and arranged to insulate said at least one closable compartment.

13. The secure climate-control system, according to claim 12 wherein said at least one insulator comprises at least one vacuum insulator structured and arranged to insulate said at least one closable compartment.

14. The secure climate-control system, according to claim 12 wherein said at least one insulator comprises at least one foam insulator structured and arranged to insulate said at least one closable compartment.

15. The secure climate-control system, according to claim 12 wherein said at least one insulator comprises at least one plastic insulator structured and arranged to insulate said at least one closable compartment.

16. The secure climate-control system, according to claim 2 further comprising at least one cover structured and arranged to cover at least said at least one closable compartment and said at least one temperature controller.

17. The secure climate-control system, according to claim 16 wherein said at least one cover comprises at least one metal.

18. The secure climate-control system, according to claim 16 further comprising at least one hinge structured and arranged to hingedly connect said at least one door with said at least one cover.

19. The secure climate-control system, according to claim 2 wherein said at least one openable access comprises at least one door.

20. The secure climate-control system, according to claim 19 further comprising at least one locking latch structured and arranged to latch and lock said at least one door.

21. The secure climate-control system, according to claim 19 further comprising at least one seal structured and arranged to seal said at least one door against said at least one closable compartment.

22. The secure climate-control system, according to claim 2 further comprising at least one container structured and arranged to contain at least one medical supplies, wherein said at least one container is adapted to be inserted into said at least one closable compartment.

23. The secure climate-control system, according to claim 22 wherein said at least one container comprises at least one lock structured and arranged to lock said at least one container.

24. The secure climate-control system, according to claim 2 wherein said at least one lock comprises:
 a) at least one electrically-actuated latch; and
 b) at least one latch controller.

25. The secure climate-control system, according to claim 24 wherein said at least one latch controller comprises:
 a) at least one electric switch adapted to actuate said at least one electrically-actuated latch;
 b) wherein said at least one electric switch is located within a first portion of the at least one wheeled emergency-response transport; and
 c) wherein said at least one electrically-actuated latch is remotely located within a second portion of the at least one wheeled emergency-response transport.

26. The secure climate-control system, according to claim 24 wherein:
 a) said at least one latch controller comprises at least one electronic device structured and arranged to control at least one locking function of said at least one electrically-actuated latch; and
 b) said at least one electronic device is structured and arrange to control such at least one locking function on receiving at least one electronic authentication.

27. The secure climate-control system, according to claim 26 wherein said at least one electronic device performs such at least one electronic authentication by receiving at least one authenticating key code from at least one keypad.

28. The secure climate-control system, according to claim 26 wherein said at least one electronic device performs such at least one electronic authentication by analyzing at least one biometric identifier.

29. The secure climate-control system, according to claim 26 wherein said at least one electronic device performs such at least one electronic authentication by acquiring authentication data from at least one data-containing device.

30. The secure climate-control system, according to claim 29 wherein said at least one data-containing device comprises at least one magnetic stripe.

31. The secure climate-control system, according to claim 29 wherein said at least one data-containing device is adapted to provide such at least one electronic authentication by wireless means.

32. The secure climate-control system, according to claim 29 wherein said at least one electronic device comprises at least one data memory adapted to store authentication data.

33. The secure climate-control system, according to claim 32 wherein said at least one electronic device comprises at least one data port adapted to permit external access to such stored authentication data by at least one portable data transfer device.

34. A method of doing business comprising the step of transporting medical supplies in at least one closable compartment of at least one secure potency-preserver, wherein said at least one secure potency-preserver is permanently installed on at least one emergency response vehicle.

35. A secure climate-control system, for preserving potency of at least one controlled substance, comprising:
 a) at least one secure potency-preserver structured and arranged to securely preserve potency of such at least one controlled substance;
 b) at least one wheeled emergency-response motor vehicle adapted to land-transport at least one emergency response worker and such at least one secure potency-preserver to emergency situations; and
 c) at least one permanent connector permanently connecting said at least one secure potency-preserver to the at least one wheeled emergency-response motor vehicle;
 d) wherein said at least one secure potency-preserver comprises:
  i) at least one closable compartment adapted to enclose at least one controlled substance;
  ii) at least one temperature controller adapted to control at least one user-definable temperature of said at least one closable compartment; and
  iii) at least one lock to lock said at least one openable access in a closed position to prevent unauthorized access to said at least one closable compartment;
  iv) wherein said at least one closable compartment comprises at least one openable access.

\* \* \* \* \*